United States Patent
Kim et al.

(10) Patent No.: US 10,098,718 B2
(45) Date of Patent: Oct. 16, 2018

(54) DENTAL SCANNER HOLDING APPARATUS AND DENTAL SCANNER SYSTEM INCLUDING THE SAME

(71) Applicants: VATECH Co., Ltd., Gyeonggi-do (KR); VATECH EWOO Holdings Co., Ltd., Gyeonggi-do (KR)

(72) Inventors: Yeong Kyun Kim, Gyeonggi-do (KR); An O Moon, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 219 days.

(21) Appl. No.: 15/034,872

(22) PCT Filed: May 20, 2015

(86) PCT No.: PCT/KR2015/005035
§ 371 (c)(1),
(2) Date: May 5, 2016

(87) PCT Pub. No.: WO2016/175368
PCT Pub. Date: Nov. 3, 2016

(65) Prior Publication Data
US 2017/0100225 A1    Apr. 13, 2017

(30) Foreign Application Priority Data
Apr. 28, 2015 (KR) ................ 10-2015-0059602

(51) Int. Cl.
*A61C 19/00* (2006.01)
*A61L 2/10* (2006.01)
(Continued)

(52) U.S. Cl.
CPC .......... *A61C 19/002* (2013.01); *A61C 1/0015* (2013.01); *A61C 9/0053* (2013.01);
(Continued)

(58) Field of Classification Search
USPC ................................................... 250/455.11
See application file for complete search history.

(56) References Cited

U.S. PATENT DOCUMENTS 5,185,532 A * 2/1993 Zabsky ............... A61C 19/002
                                                      250/455.11
5,368,171 A * 11/1994 Jackson .............. B01J 19/126
                                                             134/1
(Continued)

FOREIGN PATENT DOCUMENTS

JP       2004-097289 A      4/2004
KR       10-0457467 B1     11/2004
(Continued)

*Primary Examiner* — David A Vanore
(74) *Attorney, Agent, or Firm* — IP Legal Services, LLC

(57) ABSTRACT

The present invention relates to a dental scanner holding apparatus and a dental scanner system including the same. The apparatus may include a holding unit configured to have a dental scanner held therein, a holding detection unit configured to detect whether the dental scanner has been held in the holding unit, a humidity detection unit configured to detect humidity within the holding unit, a control unit configured to generate a sterilization signal based on a result of the detection of the holding detection unit regarding whether the dental scanner has been held in the holding unit and to generate a dehumidification signal based on the humidity detected by the humidity detection unit, an ultraviolet sterilization unit configured to radiate ultraviolet rays into the holding unit in response to the sterilization signal, and a ventilation unit configured to send air into the holding unit in response to the dehumidification signal.

3 Claims, 4 Drawing Sheets

(51) Int. Cl.
  *A61C 9/00*   (2006.01)
  *A61C 1/00*   (2006.01)
  *A61L 2/24*   (2006.01)

(52) U.S. Cl.
  CPC .................. *A61L 2/10* (2013.01); *A61L 2/24* (2013.01); *A61L 2202/14* (2013.01); *A61L 2202/24* (2013.01)

(56) References Cited

U.S. PATENT DOCUMENTS

| | | | | |
|---|---|---|---|---|
| 5,543,111 | A * | 8/1996 | Bridges | A61L 2/08 204/164 |
| 6,211,626 | B1 * | 4/2001 | Lys | A61N 5/0616 315/291 |
| 7,411,200 | B2 * | 8/2008 | Park | A61L 2/24 250/455.11 |
| 8,053,513 | B2 | 11/2011 | Gormley et al. | |
| 8,425,837 | B2 * | 4/2013 | Carbone | A61L 2/0094 422/28 |
| 8,579,163 | B2 * | 11/2013 | Ellis | A47K 5/18 206/369 |
| 8,770,881 | B2 * | 7/2014 | Dam | A61L 2/18 401/10 |
| 9,179,703 | B2 * | 11/2015 | Shur | A23L 3/003 |
| 9,592,102 | B2 * | 3/2017 | Knight | A61C 1/0076 |
| 9,707,307 | B2 * | 7/2017 | Shur | A61L 2/10 |
| 9,844,608 | B2 * | 12/2017 | Bettles | A61L 2/10 |
| 9,878,061 | B2 * | 1/2018 | Shur | A61L 2/10 |
| 2004/0202570 | A1 * | 10/2004 | Nadkarni | A61L 2/202 422/28 |
| 2005/0063194 | A1 * | 3/2005 | Lys | B60Q 1/2696 362/545 |
| 2011/0099831 | A1 * | 5/2011 | Parisi | A45D 27/48 34/92 |
| 2012/0138818 | A1 * | 6/2012 | Pugh | A61L 2/10 250/455.11 |
| 2015/0324681 | A1 * | 11/2015 | Mats | G06K 19/07766 235/492 |
| 2017/0304476 | A1 * | 10/2017 | Taggart | A61L 2/22 |

FOREIGN PATENT DOCUMENTS

| | | |
|---|---|---|
| KR | 20-0393268 Y1 | 8/2005 |
| KR | 10-2006-0002349 A | 1/2006 |
| KR | 10-1020517 B1 | 3/2011 |

* cited by examiner

DENTAL SCANNER HOLDING APPARATUS AND DENTAL SCANNER SYSTEM INCLUDING THE SAME

CROSS REFERENCE TO RELATED APPLICATIONS

This application is a National Stage Patent Application of PCT International Patent Application No. PCT/KR2015/005035 (filed on May 20, 2015) under 35 U.S.C. § 371, which claims priority to Korean Patent Application No. 10-2015-0059602 (filed on Apr. 28, 2015), the teachings of which are incorporated herein in their entireties by reference.

BACKGROUND

1. Technical Field

The present disclosure relates to a dental scanner holding apparatus and a dental scanner system including the same, and more particularly, to a dental scanner holding apparatus for automatically sterilizing and dehumidifying the tip of a dental scanner when the dental scanner is held in the dental scanner holding apparatus and a dental scanner system including the same.

2. Related Art

For dental treatment, the teeth of a patient need to be modeled in three-dimensionally accurately and more effectively. To this end, a dental scanner is required. In general, after the dental scanner is used, a sterilization process is required to prevent secondary infection between patients. In this case, the dental scanner is dipped into a solution for disinfection for a specific time without a separate sterilization device, dried, and then held in a holding stand for the dental scanner.

A conventional dental scanner system, such as that described above, may not secure perfect sterilization or dry. Accordingly, there is a problem in that secondary infection may occur.

SUMMARY

Various embodiments are directed to the provision of a dental scanner holding apparatus capable of automatically sterilizing and drying a dental scanner by only an operation for holding the dental scanner in a holding stand after the dental scanner is used and a dental scanner system including the same.

In an embodiment, a dental scanner holding apparatus for automatically sterilizing a dental scanner may include a holding unit configured to have the dental scanner held therein, a holding detection unit configured to detect whether the dental scanner has been held in the holding unit, a humidity detection unit configured to detect humidity within the holding unit, a control unit configured to generate a sterilization signal based on a result of the detection of the holding detection unit regarding whether the dental scanner has been held in the holding unit and to generate a dehumidification signal based on the humidity detected by the humidity detection unit, an ultraviolet sterilization unit configured to radiate ultraviolet rays into the holding unit in response to the sterilization signal, and a ventilation unit configured to send air into the holding unit in response to the dehumidification signal.

In this case, the dental scanner holding apparatus in accordance with an embodiment of the present invention may further include a charging unit configured to charge the dental scanner in response to a charging signal. The control unit may generate the charging signal based on a result of the detection of the holding detection unit regarding whether the dental scanner has been held in the holding unit.

The holding unit may include a first case configured to have the tip of the dental scanner received therein and a second case coupled to the first case to form a box type space in which the tip of the dental scanner is received.

The dental scanner holding apparatus may further include a water vapor detection unit configured to detect water vapor generated on the transmission window of the tip. The ventilation unit may include a heating wire configured to generate heat in response to the heat generation signal of the dehumidification signal and a ventilation fan configured to perform a rotary motion in response to the ventilation signal of the dehumidification signal. The control unit may generate the heat generation signal depending on whether water vapor detected by the water vapor detection unit has been generated.

In an embodiment, there is provided a dental scanner system including a dental scanner holding apparatus for automatically sterilizing a dental scanner. The dental scanner holding apparatus may include a holding unit configured to have the dental scanner held therein, a holding detection unit configured to detect whether the dental scanner has been held in the holding unit, a humidity detection unit configured to detect humidity within the holding unit, a control unit configured to generate a sterilization signal based on a result of the detection of the holding detection unit regarding whether the dental scanner has been held in the holding unit and to generate a dehumidification signal based on the humidity detected by the humidity detection unit, an ultraviolet sterilization unit configured to radiate ultraviolet rays into the holding unit in response to the sterilization signal, and a ventilation unit configured to send air into the holding unit in response to the dehumidification signal.

DETAILED DESCRIPTION

Figure 1:
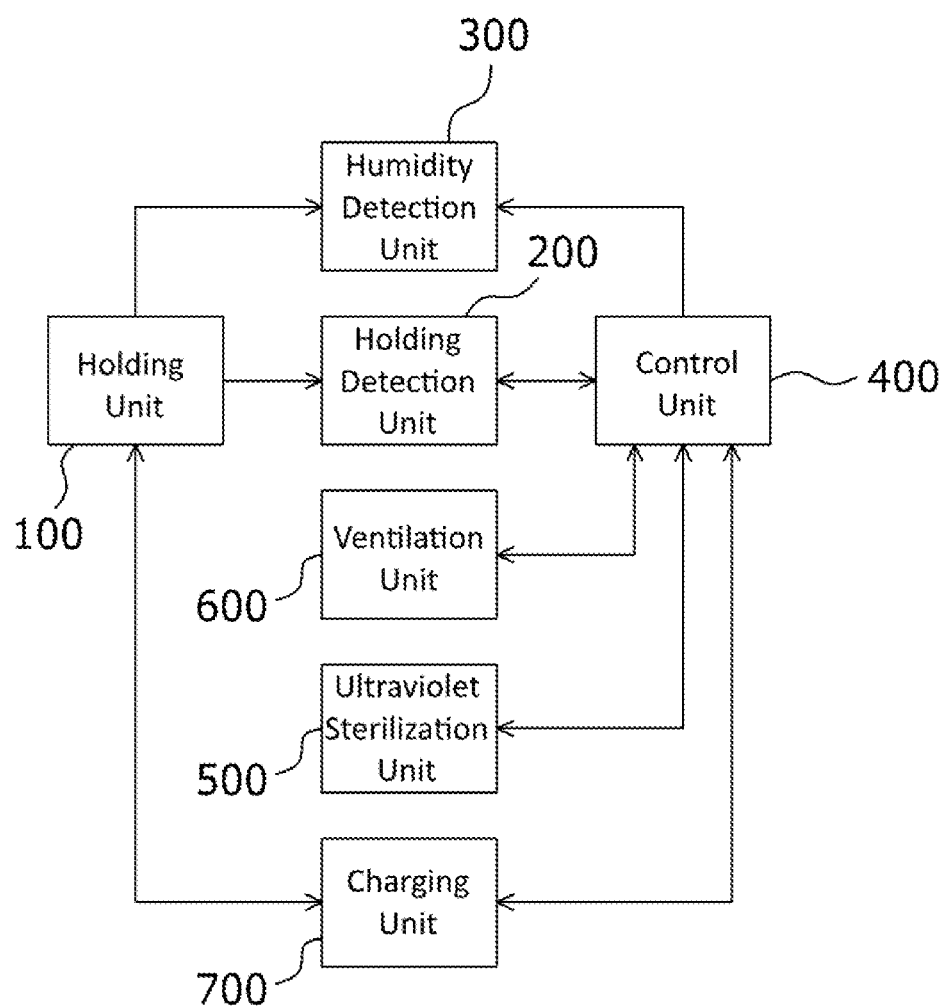
FIG. 1 is a diagram showing a scanner holding apparatus in accordance with an embodiment of the present invention.

Hereinafter, a dental scanner holding apparatus and a dental scanner system including the same will be described in detail with reference to the accompanying drawings through various examples of embodiments.

However, the embodiments of the present invention may be modified in other various forms and the scope of the present invention is not limited to the following embodiments. In the drawings, the shapes, sizes, etc. of elements may be exaggerated to make the description clear, and elements having the same reference numerals are the same elements.

The meanings of terms described in this application should be understood as follows.

Terms, such as the "first" and the "second", are used to distinguish one element from the other element, and the scope of the disclosed technology should not be restricted by the terms. For example, a first element may be named a second element. Likewise, a second element may be named a first element.

Furthermore, throughout this specification, when it is described that one part is "connected" to the other part, the one part may be "directly connected" to the other part or "electrically connected" to the other part through a third element. Furthermore, unless explicitly described to the contrary, the word "include" or "comprise", will be understood to imply the inclusion of stated elements but not the exclusion of any other elements.

Figure 2:
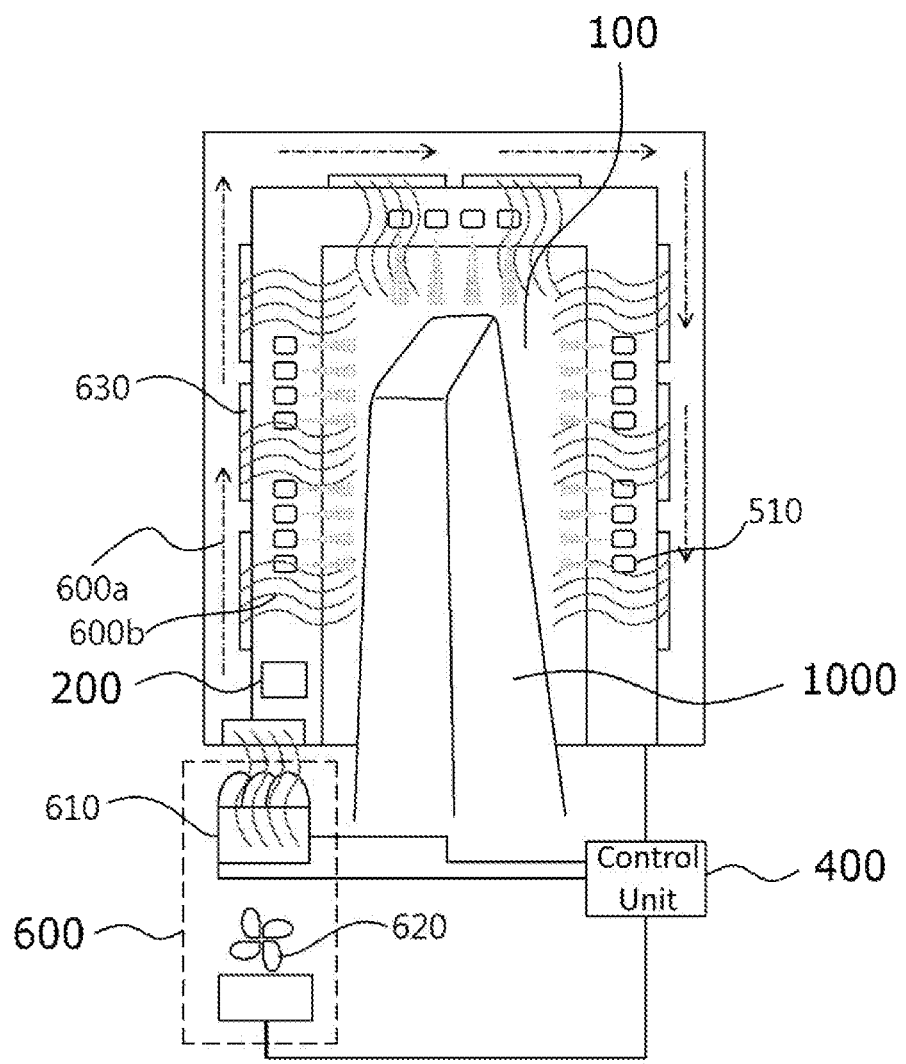
FIG. 2 is a detailed drawing showing the configuration of a dental scanner holding apparatus in accordance with an embodiment of the present invention.

FIG. 1 is a diagram showing a scanner holding apparatus in accordance with an embodiment of the present invention, and FIG. 2 is a detailed drawing showing the configuration of a dental scanner holding apparatus in accordance with an embodiment of the present invention. Referring to FIGS. 1 and 2, the dental scanner holding apparatus in accordance with an embodiment of the present invention may include a holding unit 100, a holding detection unit 200, a humidity detection unit 300, a control unit 400, an ultraviolet sterilization unit 500, a ventilation unit 600, and a charging unit 700.

A dental scanner is held in the holding unit 100. In particular, the tip (100) portion of the dental scanner may be held in the holding unit 100. In this case, the holding unit 100 may be freely formed in a size enough to accommodate the tip 1000 of the dental scanner. The holding unit 100 is not limited to a rectangular frame shape, such as that shown in FIG. 2, but may be formed in a shape, such as a cylindrical form in which the tip 1000 of the dental scanner can be received.

The holding detection unit 200 detects whether a dental scanner has been held in the holding unit 100 and outputs the results of the detection to the control unit 400. In this case, the holding detection unit 200 may be implemented in the form of a sensor formed around the holding unit 100, as shown in FIG. 2. More specifically, the holding detection unit 200 may be a pressure sensor for detecting pressure generated when the tip of the dental scanner is placed or a position detection sensor for detecting a position where the tip of the dental scanner is placed.

Furthermore, the humidity detection unit 300 detects humidity within the holding unit 100 and outputs the results of the detection to the control unit 400. That is, the humidity detection unit 300 measures internal humidity within the holding unit 100, generates a corresponding humidity signal, and outputs the generated humidity signal to the control unit 400.

The control unit 400 generates a sterilization signal based on a result of the detection of the holding detection unit 200 regarding whether the dental scanner has been held in the holding unit 100, generates a dehumidification signal based on the humidity detected by the humidity detection unit 300, outputs the generated sterilization signal to the ultraviolet sterilization unit 500, and outputs the generated dehumidification signal to the ventilation unit 600. That is, when the holding of the tip 1000 of the dental scanner is detected by the holding detection unit 200, the control unit 400 generates a sterilization signal and outputs it to the ultraviolet sterilization unit 500 so that the tip 1000 of the dental scanner is sterilized by the ultraviolet sterilization unit 500. Furthermore, when humidity detected by the humidity detection unit 300 is a specific value or more, the control unit 400 determines that the tip 1000 of the dental scanner has not been dried. Accordingly, the control unit 400 generates a dehumidification signal and outputs it to the ventilation unit 600 so that the tip 1000 of the dental scanner is dried.

Furthermore, the ultraviolet sterilization unit 500 receives a sterilization signal from the control unit 400 and radiates ultraviolet rays into the holding unit 100 in response to the received sterilization signal. That is, as shown in FIG. 2, the ultraviolet sterilization unit 500 may include a set of a plurality of ultraviolet light-emitting diodes (LEDs) 510 for radiating ultraviolet rays toward the tip 1000 of the dental scanner held in the holding unit 100.

The ventilation unit 600 receives a dehumidification signal from the control unit 400 and sends air into the holding unit 100 in response to the received dehumidification signal. That is, when the ventilation unit 600 is activated by the dehumidification signal, it sends an air 600a through a path formed in the outskirts of the dental scanner holding apparatus and sends an air 600b toward the tip 1000 of the dental scanner through one or more ventilation holes 630 formed in the holding unit 100 as shown in FIG. 2, thereby drying the tip 1000 of the dental scanner. In this case, the ventilation unit 600 may generate warm air or cold air. If humidity is not high, the ventilation unit 600 generates cold air, thereby being capable of reducing power consumption.

Furthermore, the charging unit 700 may receive a charging signal from the control unit 400 and charge the dental scanner in response to the received charging signal. That is, if the dental scanner is determined to have been held in the holding unit 100 based on the results of detection received from the holding detection unit 200, the control unit 400 generates a charging signal for charging the dental scanner and outputs the generated charging signal to the charging unit 700, thus being capable of implementing auto charging mode in which the dental scanner is automatically charged when it is held the holding unit 100. In this case, the charging unit 700 may support a wireless charging method, but the present invention is not limited thereto.

Figure 3:
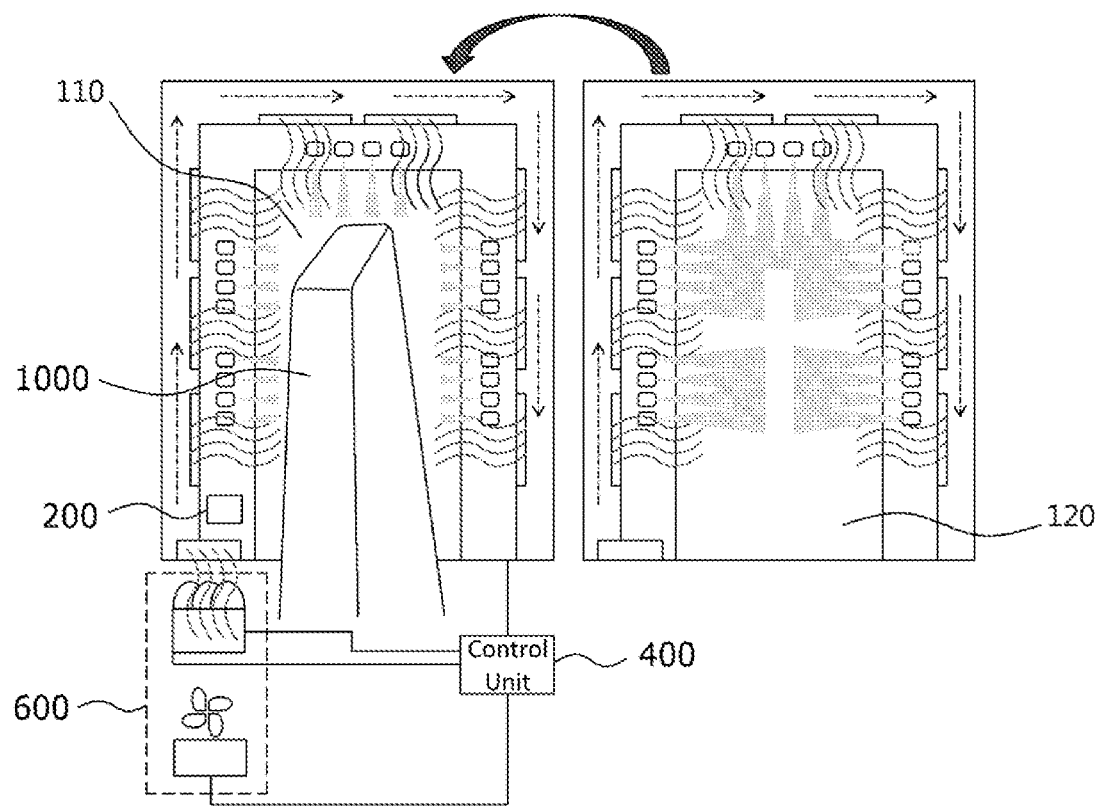
FIGS. 3 and 4 are detailed drawings showing the configuration of a dental scanner holding apparatus in accordance with another embodiment of the present invention.
Figure 4:
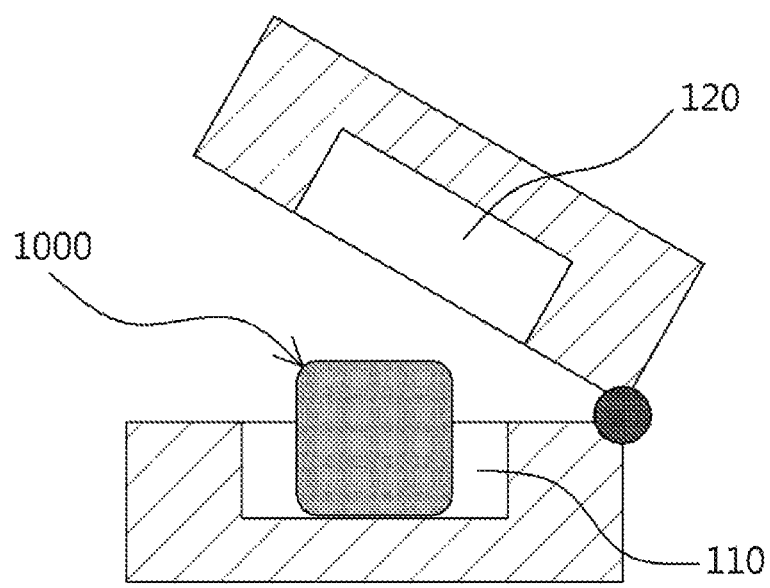

FIGS. 3 and 4 are detailed drawings showing the configuration of a dental scanner holding apparatus in accordance with another embodiment of the present invention. Referring to FIGS. 3 and 4, the holding unit 100 of the dental scanner holding apparatus in accordance with an embodiment of the present invention may include a first case 110 and a second case 120.

The first case 110 may have the tip 1000 of a dental scanner received therein and may be coupled to the second case 120, thus being capable of forming a box type space in which the tip 1000 of the dental scanner is received. That is, if the second case 120 is covered on the first case 110 using the first case 110 as a basic holding space and using the second case 120 as a cover, the tip 1000 of the dental scanner is surrounded in all directions, thereby being capable of improving dehumidification and sterilization effects. In this case, one side of the first case 110 and one side of the second case 120 may be coupled by a hinge so that the holding unit 100 is open or closed, but the present invention is not limited thereto.

Figure 5:
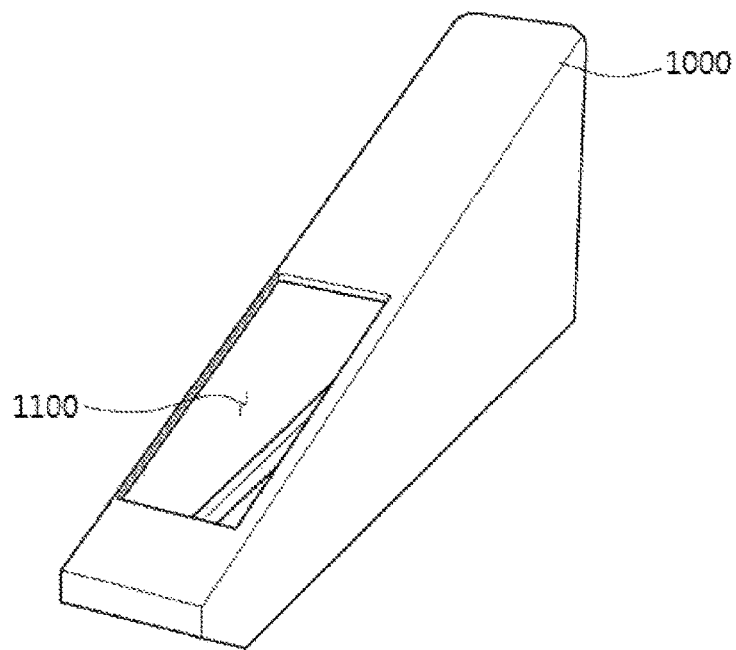
FIG. 5 is a diagram showing the tip of a dental scanner which is held in the dental scanner holding apparatus in accordance with an embodiment of the present invention.

FIG. 5 is a diagram showing the tip 1000 of a dental scanner which is held in the dental scanner holding apparatus in accordance with an embodiment of the present invention. The dental scanner holding apparatus in accordance with an embodiment of the present invention may further include a water vapor detection unit (not shown). The ventilation unit 600 may include a heating wire 610 and a ventilation fan 620.

The water vapor detection unit detects water vapor generated on a transmission window 1100 within the tip 1000 of the dental scanner and outputs the results of the detection regarding whether water vapor has been generated to the control unit 400. In this case, the water vapor detection unit is a photo sensor for detecting the inside of the holding unit 100. The water vapor detection unit may scan light on the transmission window 1100 of the tip 1000 of the dental scanner, may collect reflected light, and may detect whether water vapor has been generated based on reflectance, but the present invention is not limited thereto.

Furthermore, the heating wire 610 receives a heat generation signal, that is, a kind of a dehumidification signal, from the control unit 400 and generates heat in response to the received heat generation signal. That is, the heating wire 610 enables the ventilation unit 600 to provide warm air not an air at room temperature or cold air in order to effectively remove water vapor generated on the transmission window 1100, and may apply heat to the air 600a and 600b provided to the tip 1000 of the dental scanner.

The ventilation fan 620 receives a ventilation signal, that is, a kind of a dehumidification signal, from the control unit 400 and performs a rotary motion in response to the received ventilation signal. That is, when the ventilation fan 620 is activated by the ventilation signal, it may perform a dehumidification function by sending the air 600a and 600b to the tip 1000 of the dental scanner.

In this case, the control unit 400 may receive the results of the detection of the water vapor detection unit regarding whether water vapor has been generated. If the water vapor is determined to have been generated based on the results of the detection, the control unit 400 may generated the heat generation signal and output the generated heat generation signal to the heating wire 610.

Figure 6:
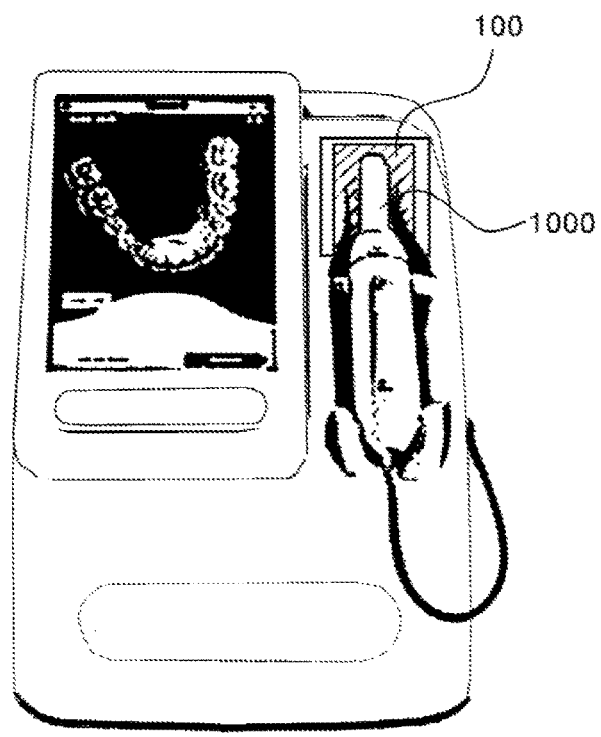
FIG. 6 is a diagram showing a dental scanner system integrated with the dental scanner holding apparatus in accordance with an embodiment of the present invention.

FIG. 6 is a diagram showing a dental scanner system integrated with the dental scanner holding apparatus in accordance with an embodiment of the present invention. Referring to FIGS. 1 to 6, the dental scanner system in accordance with an embodiment of the present invention may include the holding unit 100, the holding detection unit 200, the humidity detection unit 300, the control unit 400, the ultraviolet sterilization unit 500, the ventilation unit 600, and the charging unit 700. A description of the elements is omitted if it is redundant, and the operation of the dental scanner holding apparatus and dental scanner system shown in FIGS. 1 to 6 is described below.

First, when the tip 1000 of a dental scanner is held in the holding unit 100, the holding detection unit 200 notifies the control unit 400 of such holding. Accordingly, the control unit 400 activates the ultraviolet sterilization unit 500 by generating a sterilization signal so that a sterilization operation is performed. In this case, if the holding detection unit 200 detects that the tip 1000 of the dental scanner is no longer held in the holding unit 100, it notifies the control unit 400 that the tip 1000 is no longer held in the holding unit 100 so that the control unit 400 deactivates the remaining elements other than the holding detection unit 200. Accordingly, power consumption can be reduced.

In this case, the control unit 400 activates the humidity detection unit 300 when the holding detection unit 200 detects that the tip 1000 of the dental scanner is held in the holding unit 100. Furthermore, when the holding detection unit 200 detects that the tip 1000 of the dental scanner is held in the holding unit 100, the control unit 400 may activate the water vapor detection unit (not shown) in addition to the humidity detection unit 300.

Thereafter, if humidity within the holding unit 100 is a specific value or more, the humidity detection unit 300 notifies the control unit 400 that the humidity is the specific value or more. Accordingly, the control unit 400 activates the ventilation unit 600 by generating a dehumidification signal so that a dehumidification operation is performed. In this case, if the humidity is the specific value or more, but is not high, the control unit 400 may control the ventilation unit 600 so that it generates cold air, thereby being capable of reducing power consumption. If the humidity is high, the control unit 400 may control the ventilation unit 600 so that it generates warm air, thereby being capable of maximizing a dehumidification operation. If water vapor has been formed on the transmission window 1100 within the tip 1000 of the dental scanner, the water vapor detection unit (not shown) notifies the control unit 400 that the water vapor has been formed on the transmission window 1100. Accordingly, the control unit 400 activates the heating wire 610 of the ventilation unit 600 by generating a dehumidification signal, in particular, a heat generation signal so that the ventilation unit 600 generates warm air. Accordingly, the water vapor formed on the transmission window 1100 within the tip 1000 of the dental scanner can be removed.

In accordance with the present invention, there is an advantage in that a dental scanner can be automatically sterilized and dried by only an operation for holding the dental scanner in the holding stand after it is used.

Furthermore, when a dental scanner is held in the holding stand, the tip of the dental scanner is automatically sterilized and dehumidified. Accordingly, there is an advantage in that secondary infection which may occur when the dental scanner is held in the holding stand can be prevented without a separate sterilization device because the dental scanner is dipped into a solution for disinfection for a specific time and then dried.

While various embodiments have been described above, it will be understood to those skilled in the art that the embodiments described are by way of example only. Accordingly, the disclosure described herein should not be limited based on the described embodiments.

What is claimed is:

1. A dental scanner holding apparatus for automatically sterilizing a dental scanner, comprising:
   a holding unit configured to have the dental scanner held therein;
   a holding detection unit configured to detect whether the dental scanner has been held in the holding unit;
   a humidity detection unit configured to detect humidity within the holding unit;
   a control unit configured to generate a sterilization signal based on a result of the detection of the holding detection unit regarding whether the dental scanner has been held in the holding unit and to generate a dehumidification signal based on the humidity detected by the humidity detection unit;
   an ultraviolet sterilization unit configured to radiate ultraviolet rays into the holding unit in response to the sterilization signal;
   a ventilation unit configured to send air into the holding unit in response to the dehumidification signal; and
   a charging unit configured to charge the dental scanner in response to a charging signal, wherein the control unit generates the charging signal based on a result of the detection of the holding detection unit regarding whether the dental scanner has been held in the holding unit.

2. The dental scanner holding apparatus of claim 1, wherein the holding unit comprises:
- a first case configured to have a tip of the dental scanner received therein; and
- a second case coupled to the first case to form a box type space in which the tip of the dental scanner is received.

3. The dental scanner holding apparatus of claim 2, further comprising a water vapor detection unit configured to detect water vapor generated on a transmission window of the tip,
- wherein the ventilation unit comprises a heating wire configured to generate heat in response to a heat generation signal of the dehumidification signal and a ventilation fan configured to perform a rotary motion in response to a ventilation signal of the dehumidification signal, and
- the control unit generates the heat generation signal depending on whether water vapor detected by the water vapor detection unit has been generated.

* * * * *